United States Patent [19]

Reiff et al.

[11] Patent Number: 4,507,511
[45] Date of Patent: Mar. 26, 1985

[54] SORBITOL, PROCESS FOR ITS PREPARATION, AND USE THEREOF

[75] Inventors: Friedrich Reiff, Seeheim; Hartmut Härtner, Mühltal; Arno Basedow, Bad Vilbel; Hans-Wolfgang Hugenbusch, Höchst; Peter C. Schmidt, Marburg; Hans Bardonner, Bad König, all of Fed. Rep. of Germany

[73] Assignee: Merck Patent Gesellschaft Mit Beschränkter Haftung, Darmstadt, Fed. Rep. of Germany

[21] Appl. No.: 558,865

[22] Filed: Dec. 7, 1983

[30] Foreign Application Priority Data

Dec. 7, 1982 [DE] Fed. Rep. of Germany ....... 3245170

[51] Int. Cl.³ ...................... C07C 31/26; C07C 29/76
[52] U.S. Cl. .................................. 568/852; 568/863; 568/868; 424/52; 424/53; 426/548
[58] Field of Search ................ 568/868, 852, 863

[56] References Cited

U.S. PATENT DOCUMENTS

| 3,308,171 | 3/1967 | Oikawa | 568/868 |
| 4,252,794 | 2/1981 | DuRoss | |
| 4,292,451 | 9/1981 | de Berardinis et al. | 568/863 |
| 4,293,570 | 10/1981 | Vadasz | 568/868 |

FOREIGN PATENT DOCUMENTS

| 108005 | 9/1976 | Japan | 568/868 |
| 2046743 | 11/1980 | United Kingdom | |

Primary Examiner—J. E. Evans
Attorney, Agent, or Firm—Millen & White

[57] ABSTRACT

A modified sorbitol with improved tableting properties, viz, has a melting point of about 96° C., a bulk density of 0.3–0.6 g/ml, a γ-sorbitol content of at least 90%, a purity of at least 98%, a specific surface area of 0.7–1.5 m²/g, a bending strength of at least 7 N/mm² at a compressive force of at least 10,000 N, and a friability of less than 1% at a compressive force of at least 10,000 N, can be prepared by obtaining a sorbitol solution by hydrogenation of crystallized glucose at a temperature below 170° C., and spray-drying this solution at a temperature of 140° to 170° C. The sorbitol thus obtained has a water content of less than 1%.

The sorbitol is useful for the production of compressed formulations.

20 Claims, No Drawings

SORBITOL, PROCESS FOR ITS PREPARATION, AND USE THEREOF

BACKGROUND OF THE INVENTION

The present invention relates to a modified sorbitol having improved tableting properties, a process for preparing it, and its use in preparing compressed formulations.

Sorbitol is a tablet base which is used widely, inter alia for tablets for chewing or sucking. The particular advantage of sorbitol is that, in principle, it is even suitable for direct compression without other auxiliaries and additives. As a rule, sorbitol is obtained by hydrogenation of starch hydrolysates or by hydrogenation of invert sugar with subsequent removal of mannitol. It can be obtained in the solid form both by crystallisation and by spray-drying.

As a rule, sorbitol of this type is poorly suited for the production of satisfactory compressed products. For this reason, specific processes have been developed for the preparation of sorbitol which is more suitable for compressing. Thus, a very specific and complicated crystallisation process is described in German Pat. No. A1 3,009,875, corresponding to U.K. Pat. No. 2,046,743, by which it is possible to prepare a sorbitol suitable for compressing. Another specific crystallisation process is described in European Pat. No. A1 32,288, corresponding to U.S. Pat. No. 4,252,794.

However, these processes demand considerable industrial elaboration since the crystallisation conditions must be maintained very exactly in order to obtain a utilizable product. In addition, the products compressed from the types of sorbitol thus prepared are still not completely satisfactory in respect of bending strength and abrasion strength.

The additional use of so-called instant sorbitol obtained by spray-drying as an additive to solid, and compressed, formulations has been disclosed. However, it has not been possible to use just the instant sorbitol hitherto known, but it has been necessary to blend it with crystallized sorbitol, prepared for example by the method of German Pat. No. A1 3,009,875 or European Pat. No. A1 32,288. The use of just the instant sorbitol hitherto known led, after a short time, to adhesion to the tabletting press and thus to it becoming blocked.

OBJECTS OF THE INVENTION

One object of the present invention is to provide a modified sorbitol with improved tableting properties, especially improved bending strength and friability.

Another object of the invention is to provide a process for producing an improved sorbitol which does not require elaborate apparatus or very exact control of production conditions.

A further object of the invention is to provide an understanding of the effect of stereoisomeric hexitol impurities on tableting properties, and of how such effects can be avoided or exploited.

Upon further study of the specification and appended claims, further objects and advantages of this invention will become apparent to those skilled in the art.

SUMMARY OF THE INVENTION

These and other objects of the invention are achieved by providing a modified sorbitol with improved tableting properties, having (a) a melting point of 96° C.,
(b) a bulk density (by the method of DIN 53,912) of 0.3–0.6 g/ml,
(c) a γ-sorbitol content of at least 90%,
(d) a purity of at least 98%,
(e) a specific surface area (by the BET method) of 0.7–1.5 m$^2$/g,
(f) a bending strength of at least 7N/mm$^2$ at a compressive force of at least 10,000N, and
(g) a friability of less than 1% at a compressive force of at least 10,000N.

In a process aspect, the invention provides a process for producing a modified sorbitol having improved tableting properties, comprising the step of spray-drying a concentrated aqueous solution of sorbitol of a purity of at least 98%, at a drying gas temperature of 140°–170° C., under such conditions that the resultant spray-dried sorbitol has a moisture content of less than 1% by weight. In a further process aspect, the concentrated aqueous sorbitol solution is obtained by catalytic hydrogenation of a concentrated solution of crystallized glucose, at a temperature below 170° C.

In a method of use aspect, the invention also relates to the use of the sorbitol for the production of compressed formulations.

DETAILED DISCUSSION

It has now been found, surprisingly, that even sorbitol obtained by spray-drying (so-called "instant sorbitol") can be suitable for direct compressing and that it even provides better results than the hitherto customary sorbitol obtained by crystallization, provided that the sorbitol conforms to certain specifications, or that certain parameters are maintained in the process for its preparation.

The preparation of instant sorbitol can be controlled in such a manner that a very readily compressible product is obtained. A significant prerequisite for this is that the sorbitol be largely free of certain stereoisomeric hexitols which can be formed as by-products when sorbitol is produced by catalytic hydrogenation of hexoses, either as a consequence of the choice of the starting material for the hydrogenation or of the hydrogenation conditions themselves. Even small amounts of the isomeric sugar alcohols iditol, galactitol or talitol prevent satisfactory compressing and thus the maximum total amount of these isomers present should preferably be about 0.1% by weight.

A sorbitol solution of high purity, i.e., at least 98%, which can be used directly for spray-drying and which conforms to the foregoing prerequisites, can be conveniently prepared by, e.g., using crystallized glucose (e.g., dextrose) at the starting material for catalytic hydrogenation. It is important that the hydrogenation take place under mild conditions, i.e., at temperatures which are below about 170° C., preferably below about 160° C., e.g., 130°–150° C.

Otherwise, the hydrogenation can be carried out under conventional conditions for catalytic hydrogenations.

For this purpose, 50 to 70% glucose solutions are hydrogenated in the presence of a hydrogenation catalyst, such as, for example, a supported nickel catalyst, in particular Raney nickel, under pressures of hydrogen of about 150 to about 200 bar, in particular about 150 to 180 bar. The solution is then cooled down and the catalyst is removed. Where appropriate, the catalyst can be used again after working up. Analysis of the solutions shows that considerable amounts of by-products are already formed at temperatures of 170° C. Although these by-products do not interfere with the utilizability of the sorbitol as a sugar substitute, nevertheless, it has surprisingly emerged that these byproducts severely impair the compressibility of the sorbitol. In contrast, at hydrogenation temperatures below about 170° C. and, in particular, below about 160° C., the formation of by-products is diminished to such a great extent that it is unnecessary to crystallize, by complicated and time-consuming processes, the sorbitol from the sorbitol solution thus obtained, and it is possible to obtain it by spray-drying.

The sorbitol solution obtained from the hydrogenation solution after removal of the catalyst and desalting can be directly used for spray-drying. The content of solids is adjusted beforehand to about 65 to about 75% by weight. The spray-drying is carried out by atomisation using a centrifugal atomiser in a dry stream of gas, e.g., air, which is heated to a temperature of 140°–170° C. and blown in centrifugally. The amount of sorbitol solution introduced and that of the hot air blown in are adjusted such that the sorbitol is dried to a water content of about 0.3 to about 1% by weight. In any event, the water content should be below 1% by weight.

The particles of sorbitol which are thus obtained by the removal of water from the droplets of sorbitol are heated during the spray-drying to a temperature of about 50° to about 70° C., while the air which is blown in is cooled down to approximately the same temperature. The sorbitol is collected in containers and, after cooling down, is suitable for direct production of compressed products. Surprisingly, in contrast to the instant sorbitol previously known, the material obtained by the process according to the invention can be compressed, with the addition of small amounts of a conventional lubricant, such as, e.g., magnesium stearate, without adhesion to the tableting dies occurring.

According to the Debye-Scherrer diagram, the sorbitol according to the invention is a sorbitol which essentially consists of γ-sorbitol. In contrast to the γ-sorbitols known from German Pat. No. A1 3,009,875 and European Pat. No. A1 32,288, the sorbitol according to the invention has an irregular surface. Although spray-drying under the conditions of the invention normally produces substantially only gamma-sorbitol, the production of up to about 10% of other crystalline or amorphous forms of sorbitol will not substantially affect the advantageous properties of the resultant material.

The melting behaviour (by differential scanning calorimetry) of the sorbitol according to the invention shows a sharp peak at about 96° C. The bulk density (by the method of DIN 53,912) is about 0.3 to 0.6 g/ml, and the tamped density (by the method of DIN 53,194) is about 0.4 to 0.7 g/ml. By reason of the irregular surface, the sorbitol according to the invention has a relatively high specific surface area (by the BET method) of about 0.7 to about 1.5 m$^2$/g. The particle size can be controlled within wide limits by the spray-drying process, but as a rule is considerably lower than that of the compressible types of sorbitol previously known. Particle sizes of about 50–1000 μm can be obtained by the spray-drying process without difficulty; particle sizes of about 100–600 μm usually being preferred.

The sorbitol thus characterised has a number of advantageous tabletting properties.

Suprisingly, it can be demonstrated that, with the same compressive force, very much harder tablets can be produced with the sorbitol according to the invention than with the known compressible types of sorbitol. Since the optimum strength of tablets for sucking is determined by their behaviour on being sucked, this means that tablets of optimum hardness can be produced with only very low compressive forces. With the sorbitol according to the invention, the bending strength, which is a measure of the hardness, of tablets of 10 mm diameter and 0.3 g weight reaches a figure of about 7N/mm$^2$ at and above a compressive force of only about 10,000N, and increases further to a figure of about 11N/mm$^2$ at a compressive force above 20,000N. In contrast, a compressible sorbitol obtained by crystallization has a bending strength of only about 2.5 N/mm$^2$ at a compressive force of 10,000N, and this can only be increased to a figure of about 5N/mm$^2$ by increasing the compressive force to 20,000N. Thus, tabletting machines with which the sorbitol according to the invention is compressed can operate at relatively low compressive forces, and hence are subject to very much less wear.

Apart from the bending strength, the abrasion strength is, in particular, also crucial for the quality of the tablets. Tablets compressed from the sorbitol according to the invention have an abrasion strength of less than 1% at a compressive force of as little as 10,000N, and this decreases to an extremely low figure of about 0.2 0.3% at a compressive force of as little as 15,000N and above. In contrast, tablets made from the known compressible sorbitol have an abrasion of more than 6% at a compressive force of 5,000N, and this does not decrease to a final figure of about 1% until 15,000N is exceeded.

As already mentioned above, the strength of the tablets compressed, at the same compressive force, from the sorbitol according to the invention is very much greater than that of the tablets compressed from known forms of sorbitol. Tablets of the same strength can thus be produced with the sorbitol according to the invention using a lower compressive force and accordingly they have a markedly greater volume than otherwise comparable tablets. Since, at constant tablet strength, the duration of sucking corresponds to the volume of the tablet, using the sorbitol according to the invention, tablets can be produced which have a considerably lower weight for the same duration of sucking. It is possible by this means to achieve considerable savings in material.

By reason of its irregular surface, the sorbitol according to the invention is also able to bind relatively large amounts of additives, such as, for example, cocoa powder, colourants and other additives. Its absorbing capacity is considerably higher than that of the known compressible types of sorbitol. Even with large amounts of additives, e.g., up to about 20 parts by weight per 100 parts by weight of sorbitol, homogeneous mixtures are obtained, and the compressed products which are produced therefrom have a uniform appearance.

Because of the particular mode of preparation, by spray-drying an aqueous solution, it is possible to distribute water-soluble additives, such as, for example, colourants, vitamins and the like, completely homogeneously in the sorbitol or the compressed products which are produced therefrom.

In contrast to tablets which have been obtained by admixing a colourant to crystallized sorbitol before tableting and which exhibit a mottled surface, tablets produced according to the invention have a surface of a completely uniform colour.

As already mentioned, the sorbitol according to the invention can be directly compressed merely with the addition of small amounts of a conventional lubricant, such as, e.g., 0.3 to 2% by weight of magnesium stearate. The only essential point is that the water content which, by reason of the process of preparation according to the invention, is about 0.3 to about 1% by weight, does not rise to figures above about 1% by storage for too long at high humidity. It is true that types of sorbitol having higher water contents can still be satisfactorily compressed in rooms of relatively low humidity, but, on being compressed in rooms of high humidity, they tend to adhere to the press dies.

Moreover, good compressibility is not impaired on admixture of additives, such as, for example, colourants, flavourings or pharmaceutical agents by which the appearance, taste and spectrum of action of the formulation can be affected.

As already mentioned above, the purity of the sorbitol according to the invention should be greater than about 98%, since it has been shown that certain impurities can have a very adverse effect on the tabletting properties.

However, on the other hand, it has been demonstrated, that it is possible, by using certain additives, even to increase the tablet strength which is in any case very good. Thus, surprisingly, and in contrast to the effect of other stereoisomeric hexitols, by admixing mannitol in an amount of about 10 to 15% by weight, relative to the weight of sorbitol, before or after spray-drying, a product is obtained which reaches a bending strength above $15N/mm^2$ at a compressive force above as little as 15,000N. Thus, an additional aspect of the present invention which is particularly advantageous is formulations of sorbitol which contain up to 15% by weight, e.g., 1–15% of mannitol.

The sorbitol according to the invention can be used alone or with additives for all usual purposes, in particular for the production of tablets for chewing or sucking. By reason of the improved tabletting properties, the invention achieves a considerable advance in this area.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

50 g of moist Raney nickel are added to a solution of 750 g of crystallized dextrose in 500 ml of deionized water in a 2 liter high-pressure autoclave and hydrogenation is carried out at 130° C. and 150 bar until uptake of hydrogen is complete. After cooling down the suspension the catalyst is filtered off with suction and washed with water.

The solids in the solution consist of 99.2% by weight of sorbitol. By-products are only present in insignificant traces. The resultant solution, having a solids content of about 60% by weight, is spray-dried in a centrifugal atomizer with a stream of air at 150° C. The sorbitol obtained essentially consists of the γ-form and has 0.8% by weight of residual moisture, a melting point of 96° C., a bulk density of 0.4 g/ml, a specific surface area (by the BET method) of $1.0 m^2/g$, and a mean particle size (α' value in the RRSB distribution) of 500 μm, 90% of the particles being in the range 280 to 620 μm. On compressing the sorbitol with the addition of 0.3% by weight of magnesium stearate to give tablets weighing 300 mg and of diameter 10 mm on an eccentric press, the following results are obtained:

| Compressive force (N) | 10,000 | 20,000 | 30,000 |
| --- | --- | --- | --- |
| Tablet thickness (mm) | 3.02 | 2.77 | 2.74 |
| Bending strength ($N/mm^2$) | 8.5 | 12.5 | 12.5 |
| Friability (%) | 0.4 | 0.2 | 0.2 |

The bending strength is determined using a modified hardness tester supplied by Erweka, Heusenstamm, F.R.G., by the method described in P.H. List: Arzneiformenlehre (Drug Formulations) 3rd edition, page 105, Wiss. Verlagsgesellschaft mbH, Stuttgart, 1982, the gap between the supports being 6.7 mm.

The friability is determined in a Friabilator supplied by Erweka, Heusenstamm, F.R.G., with a running time of 6 min.

EXAMPLE 2

Hydrogenation is carried out in accordance with Example 1, but at a temperature of 150° C. The solids in the resultant solution consist of 98.7% by weight of sorbitol. Again, by-products are present in only insignificant amounts. The product obtained by spray-drying according to Example 1 can be compressed without problems, results being obtained which are analogous to those given in Example 1.

COMPARATIVE EXAMPLE 3

Hydrogenation is carried out according to Example 1, but at a temperature of 170° C. The solids in the resultant solution consist of only 95.9% by weight of sorbitol. The by-products contained therein make the product which is obtained after spray-drying according to Example 1 unsuitable for direct compressing although the material could be used directly as a sugar substitute.

COMPARATIVE EXAMPLE 4

35 kg of Raney nickel are added to a solution of 750 kg of crystallized dextrose in 500 liters of water and hydrogenation is carried out at 180° C. and under a pressure of 150 bar. The solution which, after the uptake of hydrogen is complete, is cooled down and filtered contains solids which consist of 94.1% by weight of sorbitol.

The numerous by-products make the product obtained by spray-drying according to Example 1 unsuitable for direct compressing, although this product would also be readily utilizable as a sugar substitute.

A sorbitol prepared by the method of Example 1 or Example 2 can be employed in the use examples which follow.

EXAMPLE 5

Tablets for Oral Hygiene

Instant sorbitol: 96.0 parts by weight
Magnesium peroxide: 2.0 parts by weight
Peppermint oil: 1.5 parts by weight Magnesium stearate: 0.5 parts by weight The constituents are mixed and compressed, to form tablets of diameter 6 mm and weighing 100 mg, under a pressure of 6,000N.

EXAMPLE 6

Menthol Tablets

Instant sorbitol: 247.0 parts by weight
Menthol: 1.8 parts by weight
Magnesium stearate: 1.2 parts by weight The constituents are mixed and compressed, to form tablets of diameter 9 mm and weighing 250 mg, under a pressure of 14,000N.

EXAMPLE 7

Tablets for Caries Prophylaxis

Instant sorbitol: 98.34 parts by weight
Sodium fluoride: 1.16 parts by weight
Magnesium stearate: 0.5 parts by weight The constituents are mixed and compressed, to form tablets of diameter 7 mm and weighing 100 mg, under a pressure of 8,000N.

EXAMPLE 8

Sorbitol Tablets for Sucking

Instant sorbitol: 491.0 parts by weight
Citric acid: 5.0 parts by weight
Dried fruit flavour:
(various types): 1.5 parts by weight
Magnesium stearate: 2.5 parts by weight The constituents are mixed and compressed, to form tablets of diameter 13 mm and weighing 500 mg, under a pressure of 30,000N.

EXAMPLE 9

Vitamin C Tablets

Instant sorbitol: 447.0 parts by weight
Ascorbic acid: 50.0 parts by weight
Dried lemon flavour: 0.5 parts by weight
Magnesium stearate: 2.5 parts by weight The constituents are mixed and compressed, to form tablets of diameter 13 mm and weighing 500 mg, under a pressure of 30,000N.

EXAMPLE 10

Coffee-flavoured Tablets

Instant sorbitol: 462.5 parts by weight
Powdered coffee extract: 25.0 parts by weight
Caffeine: 10.0 parts by weight
Magnesium stearate: 2.5 parts by weight The constituents are mixed and compressed, to form tablets of diameter 13 mm and weighing 500 mg, under a pressure of 30,000N.

EXAMPLE 11

Cocoa-flavoured Tablets

Instant sorbitol: 449 parts by weight
Cocoa powder: 50 parts by weight
Citric acid: 1 part by weight The constituents are mixed and compressed, to form tablets of diameter 13 mm and weighing 500 mg, under a pressure of 30,000N.

It is also possible to use, in all compositions indicated, instant sorbitol which has been sweetened with 0.1% of saccharin or 0.2% of aspartame, or instant sorbitol which has been coloured.

The preceding example(s) can be repeated with similar success by substituting the generically or specifically described reactants and/or operating conditions of this invention for those used in the preceding example(s).

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A modified sorbitol with improved tableting properties, having
   (a) a melting point of about 96° C.,
   (b) a bulk density of 0.3–0.6 g/ml,
   (c) a $\gamma$-sorbitol content of at least 90%,
   (d) a purity of at least 98%,
   (e) a specific surface area of 0.7–1.5 $m^2/g$,
   (f) a bending strength of at least 7N/$mm^2$ at a compressive force of at least 10,000N, and
   (g) a friability of less than 1% at a compressive force of at least 10,000N.

2. The modified sorbitol of claim 1, having a moisture content of less than 1% by weight.

3. The modified sorbitol of claim 1, wherein the total content of iditol, galactitol and talitol is at most 0.1% by weight.

4. The modified sorbitol of claim 1, having a tamped density of 0.4–0.7 g/ml.

5. The modified sorbitol of claim 1, having a friability of about 0.2–0.3% at a compressive force of at least 15,000N.

6. A process for producing a modified sorbitol having improved tableting properties, comprising the step of spray-drying a concentrated aqueous solution of sorbitol of a purity of at least 98%, at a drying gas temperature of 140°–170° C., under such conditions that the resultant spray-dried sorbitol has a moisture content of less than 1% by weight.

7. The process of claim 6, wherein the drying gas is air.

8. The process of claim 6, wherein the spray-drying is effected by atomisation using a centrifugal atomiser.

9. The process of claim 6, wherein the concentrated sorbitol solution has a solids content of about 65–75% by weight.

10. The process of claim 6, wherein said concentrated aqueous sorbitol solution is obtained by catalytic hydrogenation of a concentrated solution of crystallized glucose, at a temperature below 170° C.

11. The process of claim 10, wherein the temperature for said hydrogenation is below 160° C.

12. The process of claim 11, wherein said temperature is 130°–150° C.

13. The process of claim 10, wherein the catalyst is Raney nickel.

14. The process of claim 10, wherein the hydrogenation is effected at a hydrogen pressure of 150–200 bar.

15. In a process for producing compressed formulations, wherein sorbitol is used as a base, the improvement wherein the sorbitol is a modified sorbitol according to claim 1.

16. In a process for producing compressed formulations, wherein sorbitol is used as a base, the improvement wherein the sorbitol is the modified sorbitol of claim 15.

17. The modified sorbitol of claim 1 produced by a process comprising the step of spray-drying a concentrated aqueous solution of sorbitol of a purity of at least 98%, at a drying gas temperature of 140°–170° C., under such conditions that the resultant spray-dried sorbitol has a moisture content of less than 1% by weight.

18. The modified sorbitol of claim 17 wherein the concentrated sorbitol solution has a solids content of about 65–75% by weight.

19. The modified sorbitol of claim 18 wherein said concentrated aqueous sorbitol solution is obtained by catalytic hydrogenation of a concentrated solution of crystallized glucose, at a temperature below 170° C.

20. The modified sorbitol of claim 19 wherein the temperature of hydrogenation is 130°–150° C., the catalyst is Raney nickel and the hydrogenation is conducted under a hydrogen pressure of 150–200 bar.

* * * * *